(12) United States Patent
Patterson et al.

(10) Patent No.: US 8,043,565 B1
(45) Date of Patent: Oct. 25, 2011

(54) ANALYTICAL INSTRUMENTATION AND PROCESSES

(75) Inventors: Garth E. Patterson, Brookston, IN (US); Mark Gregory, Lafayette, IN (US)

(73) Assignee: Griffin Analytical Technologies, L.L.C., West Lafayette, IN (US)

( * ) Notice: Subject to any disclaimer, the term of this patent is extended or adjusted under 35 U.S.C. 154(b) by 972 days.

(21) Appl. No.: 11/433,240

(22) Filed: May 12, 2006

Related U.S. Application Data (60) Provisional application No. 60/681,188, filed on May 13, 2005.

(51) Int. Cl.
  *G01N 30/02* (2006.01)
  *B01L 9/06* (2006.01)
  *G01N 30/04* (2006.01)
  *B01L 3/00* (2006.01)

(52) U.S. Cl. .......... 422/89; 422/500; 422/560; 422/562; 73/23.35; 73/23.39; 73/23.42; 436/161

(58) Field of Classification Search .......... None
See application file for complete search history.

(56) References Cited

U.S. PATENT DOCUMENTS

| | | | |
|---|---|---|---|
| 3,440,397 A | 4/1969 | Vesper et al. | |
| 3,449,938 A | 6/1969 | Giddings et al. | |
| 4,650,964 A | 3/1987 | Vincent | |
| 4,726,822 A | 2/1988 | Cates et al. | |
| 4,805,441 A | 2/1989 | Sides et al. | |
| 4,854,952 A | 8/1989 | Stepien | |
| 4,948,389 A | 8/1990 | Klein et al. | |
| 5,014,541 A | 5/1991 | Sides et al. | |
| 5,096,471 A | 3/1992 | Sacks et al. | |
| 5,108,705 A | 4/1992 | Rounbehler et al. | |
| 5,114,439 A | 5/1992 | Yost et al. | |
| 5,236,668 A * | 8/1993 | Higdon | 422/89 |
| 5,551,278 A | 9/1996 | Rounbehler et al. | |
| 5,589,630 A | 12/1996 | Wiegand et al. | |
| 5,611,846 A | 3/1997 | Overton et al. | |
| 5,665,314 A * | 9/1997 | Berger et al. | 422/89 |
| 5,782,964 A | 7/1998 | Mustacich | |
| 5,808,178 A | 9/1998 | Rounbehler et al. | |
| 5,856,616 A * | 1/1999 | Maswadeh et al. | 73/23.42 |
| 6,209,386 B1 | 4/2001 | Mustacich et al. | |
| 6,217,829 B1 | 4/2001 | Mustacich et al. | |
| 6,223,584 B1 | 5/2001 | Mustacich et al. | |
| 6,427,522 B1 | 8/2002 | Thomas et al. | |
| 6,490,852 B1 | 12/2002 | Mustacich et al. | |
| 6,530,260 B1 | 3/2003 | Mustacich et al. | |
| 6,682,699 B2 | 1/2004 | Mustacich et al. | |

* cited by examiner

*Primary Examiner* — Jill Warden
*Assistant Examiner* — Neil N Turk
(74) *Attorney, Agent, or Firm* — Wells St. John P.S.

(57) ABSTRACT

Gas chromatography apparatuses are provided that can include a housing configured to substantially envelop the column within the compartment. Analytical instruments are provided that can include at least one chromatography column compartment having a volume of the less than 100 mL. Analytical methods are provided that can include increasing the temperature of a chromatography column at a rate of about 60° C./minute using less than about 40 W. Methods are also provided that include providing at least one gas chromatography column compartment configured to substantially envelop a gas chromatography column and performing analysis with the one compartment in the first operable position and/or transitioning portions to the second operable position to allow access to the one compartment. Production processes are provided that can include forming a first trench within the first surface of a substrate and/or aligning the first substrate with a second substrate to define at least one compartment between the first and second substrates.

5 Claims, 9 Drawing Sheets

ANALYTICAL INSTRUMENTATION AND PROCESSES

RELATED PATENT DATA

This patent application claims priority under 35 U.S.C. §119 of U.S. provisional patent application Ser. No. 60/681,188 entitled Analytical Instrumentation and Processes filed May 13, 2005, the entirety of which is incorporated by reference herein.

TECHNICAL FIELD

The present disclosure provides analytical instrumentation and processes and in particular embodiments provides gas chromatography apparatuses, analytical methods, and apparatus production processes.

BACKGROUND OF THE DISCLOSURE

Gas chromatography has been used as a separation and analysis technique for the detection of chemical warfare agents, environmental contaminants, and/or explosive compounds. Chromatographic separation can be based on the differential partitioning of compounds between a stationary phase coated on the inside of a capillary column and what can be referred to as the mobile phase such as carrier gas. Compounds that partition into the stationary phase can be retained longer within the column than other compounds that remain in the mobile phase. Compounds that partition into the stationary phase will therefore reach a detector at the end of the column later than will the other compounds that remain in the mobile phase as the other compounds are not as restrained as the compounds in the stationary phase. Temperature can be used to change the partitioning of compounds between the stationary and mobile phases, which can result in the separation of similar compounds. Gas chromatography can be highly reproducible and/or quantitative resulting in the ability to analyze complex samples rapidly.

However, the use of gas chromatography as an analytical tool can be limited by the requirement of a large, temperature-controlled oven. Typical laboratory based systems are quite large (24×24×30 inches, for example) and require significant power (~1000 W). There have been many attempts at size and power reduction of gas chromatography systems. For example, ABB (www.ABB.com) manufactures the ACAMS for detection of chemical warfare agents at government facilities. OI Analytical (151 Graham Road, College Station, Tex. 77845) sells the mini-CAMS for the same purpose.

SUMMARY OF THE DISCLOSURE

Gas chromatography apparatuses are provided that can include a housing defining at least one compartment therein. The one compartment can be configured to receive a gas chromatography column, and the housing can be configured to substantially envelop the column within the compartment. First and second connectors can also be coupled to the housing. The first connector can be configured to couple a sample preparation component to the column within the one compartment, and the second connector can be configured to couple a detection component to the column within the one compartment. The apparatuses can include a plurality of vents extending from exterior portions of the housing to the one compartment.

Analytical instruments are provided that can include a sample preparation component coupled to a gas chromatography apparatus, and a detector component coupled to the gas chromatography apparatus. The chromatography apparatus can include a housing defining at least one chromatography column compartment, with the volume of the one compartment being less than 100 mL.

Analytical methods are provided that can include providing a sample to a gas chromatography column with the sample including a plurality of components. Methods provide for increasing the temperature of the column at a rate of about 60° C./minute using less than about 40 W to separate one of the components from at least one other component of the sample.

Analytical methods are also provided that can include providing at least one gas chromatography column compartment configured to substantially envelop a gas chromatography column. The one compartment can be comprised of at least a first portion operably coupled to a second portion with the portions defining the one compartment in a first operable position and allowing access to the one compartment in a second operable position. Methods provide for performing analysis with the one compartment in the first operable position and/or transitioning the portions to the second operable position to allow access to the one compartment.

Production processes are provided that can include providing a first substrate comprising a first surface extending to opposing edges. Processes provide for forming a first trench within the first surface and/or aligning the first substrate with a second substrate to define at least one compartment between the first and second substrates. The one compartment can be configured to substantially envelop a gas chromatography column.

BRIEF DESCRIPTION OF THE DRAWINGS

Preferred embodiments of the invention are described below with reference to the following accompanying drawings.

DETAILED DESCRIPTION OF THE DISCLOSURE

Figure 1:
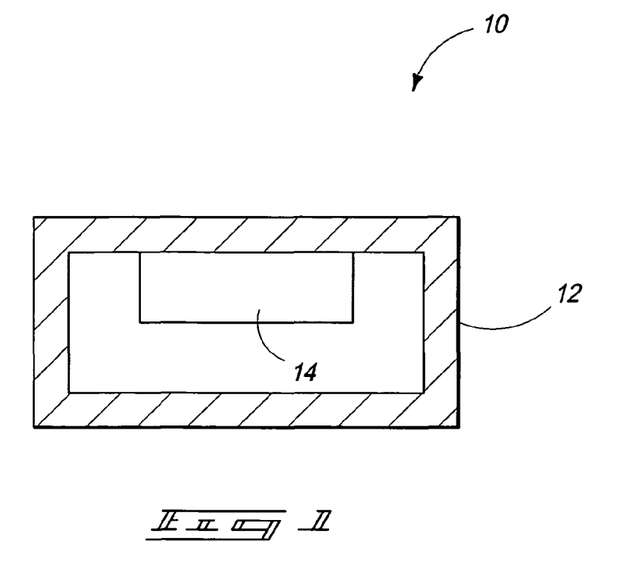
FIG. 1 is an illustrative view of an instrument according to an embodiment.

At least some embodiments provide analytical apparatuses, instrumentation, processes, and methods, as well as production processes. Exemplary configurations are described with reference to FIGS. 1-11. Referring to FIG. 1, instrument 10 is shown that includes a support structure 12 and analytical components 14. In exemplary embodiments, support structure 12 can house analytical components 14. Support structure 12 can include a fabricated housing such as fabricated aluminum, for example. Analytical components 14 can be configured to provide analytical data. According to exemplary embodiments, instrument 10 can be configured as described in U.S. patent application Ser. No. 10/570,706 entitled Analysis Device Operational Methods and Analysis Device Programming Methods, filed Mar. 3, 2006, the entirety of which is incorporated by reference herein. Instrument 10 may also be configured as described in U.S. patent application Ser. No. 10/570,707 entitled Mass Spectrometry Methods and Devices, filed Mar. 3, 2006, the entirety of which is incorporated by reference herein.

Exemplary analytical data can include both qualitative and quantitative data, such as the identification and quantitation of chemical compounds.

Instrument 10 can be configured as described in U.S. patent application Ser. No. 10/542,187 entitled Mass Spectrometer Assemblies, Mass Spectrometry Vacuum Chamber Lid Assemblies, and Mass Spectrometer Operational Methods filed Jul. 13, 2005, the entirety of which is incorporated by reference herein. Instrument 10 can also be configured as described in U.S. patent application Ser. No. 10/554,039 entitled Mass Spectrometry Instruments and Methods, filed Oct. 20, 2005, the entirety of which is incorporated by reference herein. As another example, instrument 10 can be configured as described in International Patent Application Serial No. PCT/US05/20783 entitled Analytical Instruments, Assemblies, and Methods, filed Jun. 13, 2005, the entirety of which is incorporated by reference herein.

Figure 2:
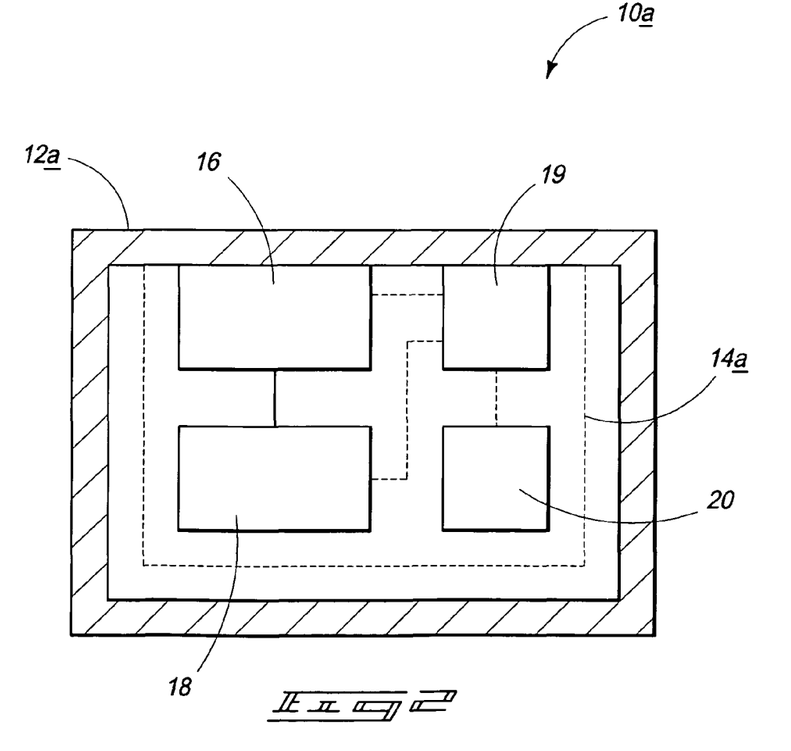
FIG. 2 is an illustrative view of the instrument of FIG. 1 according to an embodiment.

Referring to FIG. 2, exemplary instrument 10a is shown that includes analytical components 14a housed within structure 12a. Instrument 10a, analytical components 14a, as well as structure 12a are exemplary of instrument 10, analytical components 14, and structure 12. Components 14a can include sample introduction component 16 coupled to detection component 18. Analytical components 14a can also include a power supply 20 coupled to processing and control components 19. Exemplary power supply 20 can include portable batteries such as sealed lead, acid and/or lithium iron or polymer batteries. In exemplary embodiments, structure 12a can house analytical components 14a including power supply 20. In other embodiments power supply 20 may be located outside the space defined by the structure 12a. In exemplary implementations, instrument 10a can be less than 20 lbs in weight. Instrument 10a can be configured as a mass spectrometer and in such configurations instrument 10a can be less than 50 lbs in weight, for example. Instrument 10a may also be person portable and/or be operable on battery supply.

Sample introduction component 16 can include a sample introduction port (not shown) coupled to structure 12a and at least one sample preparation component (not shown). Exemplary sample introduction components can include those described in U.S. patent application Ser. No. 11/173,263 entitled Spectrometry Instruments, Assemblies and Methods, filed Jun. 30, 2005, the entirety of which is incorporated by reference herein. Component 16 can also be configured as described in U.S. patent application Ser. No. 11/152,395 entitled Instrument Assemblies and Analysis Methods, filed Jun. 13, 2005, the entirety of which is incorporated by reference herein. Sample introduction ports can be configured to receive a sample for analysis.

The sample can represent any chemical composition, including both inorganic and organic substances, in solid, liquid and/or vapor form. Specific examples of the sample suitable for analysis include volatile compounds such as toluene or other specific examples including non-volatile structures such as trinitrotoluene (TNT). Samples can also include toxic compounds and/or chemical warfare agents. In certain aspects, the sample can be a mixture containing more than one substance or in other aspects the sample can be a substantially pure substance. Analysis of the sample can be performed according to exemplary aspects described below. Exemplary introduction component 16 can be configured to receive the sample and convey the sample to sample preparation components.

In an exemplary aspect, the sample introduction port can be configured to receive sample via manual introduction, such as manual introduction via a syringe, and in other aspects, the sample introduction port can be configured to receive sample via automated introduction, such as an auto-sampler. Other exemplary implementations include component 16 being configured to acquire and/or receive gas-phase samples. Such exemplary gas-phase sampling devices can be configured to acquire a known quantity of atmosphere, for example.

For example and by way of example only, component 16 can include a sample inlet port configured to convert the sample to a form suitable for transfer. For example, a solid sample can be converted to a liquid and/or a gas, or a liquid sample can be converted to a gas and/or a solid. Likewise, gases may be converted to liquids and/or solids depending on the configuration of instrument 10a. Types of sample inlet ports include batch inlets, direct probe inlets, and permeable, semi-permeable, solid phase microextraction (SPME) and/or capillary membrane inlets, as well as continuous sampling ports. Sample inlet ports can also include liquid injection ports that can be configured to be operated in split and splitless modes. Exemplary ports include thermal desorber systems.

Component 16 can be configured to utilize different sample introduction ports simultaneously. For example, the sample introduction port can be configured, in one embodiment, as parallel ports with one port configured to receive sample from a syringe and another port configured to receive sample from another instrument such as an automated air sampling device.

Depending upon the sample, component 16 may also be configured to prepare the sample for introduction into remaining components 14a. According to the exemplarily depicted embodiment of FIG. 2, component 16 can be configured to prepare the sample for introduction into detection component 18. Component 16 can also include sample preparation components that can be configured to prepare the sample received from a sample introduction port, for example, for analysis by the remaining components 14a. Component 16 can include the sample preparation components and these sample preparation components can be coupled to the remaining components 14a. According to exemplary embodiments, some of the remaining analysis components 14a can be directly coupled to the sample introduction port. For example, an analysis component of components 14a, such as a sample preparation component, can be configured to receive the sample from the batch inlets, direct probe inlets, SPME, and/or capillary membrane inlets described above. The sample preparation component can be configured to separate the sample through, for example, chromatography. For example, component 16 can be configured to pass the sample through a gas chromatography apparatus. In exemplary embodiments, the gas chromatography apparatus can include capillary columns and in other embodiments, the apparatus can be configured to perform fast gas chromatography. Chromatography apparatus such as that manufactured by RVM Scientific (5511 Ekwill St. #A, Santa Barbara, Calif. 93111-2398) can be utilized. The apparatus can be of a low-thermal-mass that eliminates the large air bath gas oven and is therefore capable of providing very rapid temperature ramps.

The chromatography apparatus can be powered by power supply 20, while providing standard temperature profiles using process and control components 19. In exemplary embodiments, the power utilized is low when compared to that of conventional ovens. Chromatography apparatus such as that manufactured by RVM Scientific have been modified to couple to mass spectrometers such as the Minotaur 300 manufactured by Griffin Analytical Technologies (West Lafayette, Ind.). In exemplary embodiments, instrument 10a can be the size of a tower computer, can weigh about 40 lbs. and can include all of the required components of a gas chromatograph coupled to a mass spectrometer (GC-MS). Instrument 10a can consume ~250 W (dependent upon configuration) and can be operated on battery power for ~1 hour. In exemplary embodiments, rapid chromatographic separation and multi-dimensional mass analysis can be achieved using instrument 10a.

The RVM chromatographic apparatus is manufactured as an integrated assembly. The integrated assembly includes the gas chromatography column (the most common replacement component), a heater, and a temperature control line, for example, and replacement of one of these components requires the replacement of the entire assembly. For example, when changing and/or maintaining columns of the RVM apparatus, the entire assembly requires replacement instead of the column itself. Replacing components additional to the column can increase the cost of performing this routine replacement and/or maintenance work by at least a factor of five over the cost of replacing and/or maintaining the gas chromatography column alone.

Furthermore, the RVM apparatus does not provide analysts with the flexibility to change chromatographic columns inexpensively as analysis dictates. For example, one sample may dictate analysis with one column and another sample with another column. The integrated assembly requires the analyst have two assemblies on hand; one having one column, and another having another column. As such the analyst is required to have an additional assembly available that costs 4 to 5 times more than an off-the-shelf column because the analyst cannot replace the column of the integrated assembly with one of his own choosing.

The integrated assembly can further complicate matters such as maintenance. For example, gas chromatography columns can become clogged and require the removal of a portion of the column to remove the clog, typically the portion proximate the inlet assembly. An integrated assembly does not allow for such removal and, as such, the entire assembly requires replacement, instead of a relatively simple removal of a portion of the column that has little, if any, impact on separation performance.

Component 16 can include a consumables generator. In exemplary embodiments, the consumables generator can be configured to generate consumables for use during the operation of the instrument. For example, where the sample preparation component is configured to process the sample by gas chromatography, the consumables generator can be configured to provide carrier gas to the gas chromatograph. In exemplary embodiments the generator is configured as a nitrogen generator and nitrogen is utilized as a carrier gas during the gas chromatography performed by component 16. Exemplary aspects also include a generator configured to provide consumables to the sample introduction port. For example, in the case where the port is configured to be flushed either before or after the sample is received, the generator can be configured to provide flushing gases to the port. In exemplary embodiments the generator can be external or internal of the instrument. Exemplary aspects also include providing consumables from outside the instrument, such as configuring the instrument to be coupled to a tank of consumable carrier gas.

Detection components 18 can include exemplary gas chromatography detection components, such as flame ionization, thermal conductivity, and/or photo ionization detection components as well as mass detection components including mass spectrometry detection components. In exemplary embodiments, the detection components may require vacuum components such as getter pumps, piston pumps, turbo pumps, and/or drag pumps. In exemplary embodiments, rugged pumps capable of providing sufficient vacuum can be utilized. The vacuum component can include both a high vacuum pump and a rough pump. In exemplary implementations, the rough pump and high vacuum pump can be configured to share common components such as circuitry and/or power supply. High vacuum pumps such as turbo pumps can be backed by a rough pump such as a diaphragm pump or rotary vane pump, for example.

In exemplary embodiments, detection components 18 are configured to be modular thereby facilitating sufficient maintenance and/or removal and replacement. Exemplary detection components include those described in U.S. patent application Ser. No. 10/537,019 entitled Processes for Designing Mass Separators and Ion Traps, Methods for Producing Mass Separators and Ion Traps, Mass Spectrometers, Ion Traps, and Methods for Analyzing Samples, filed Jun. 1, 2005, the entirety of which is incorporated by reference herein. Additional detection components include those described in International Patent Serial No. PCT/US04/29127 entitled Ion Detection Methods, Mass Spectrometry Analysis Methods, and Mass Spectrometry Instrument Circuitry, filed Sep. 3, 2004, the entirety of which is incorporated by reference herein.

Processing and control components 19 can be coupled to inlet system 16, detection components 18, and power supply 20 components as shown in FIG. 2, for example. All the components described above can be controlled, monitored, and/or have data acquired from by processing and control components 19. In exemplary embodiments all or at least more than one of the components described above can be coupled to processing and control components 19. According to exemplary embodiments, instrument 10a and processing and control components 19 can be configured to perform analysis using apparatuses and methods described in International Patent Application Ser. No. 11/919,323 filed May 10, 2006 entitled Analytical Instrumentation, Apparatuses and Methods, the entirety of which is incorporated by reference herein.

Processing and control components 19 can include a user interface coupled to structure 12a of instrument 10a, for example. Processing and control components 19 can also include processing circuitry coupled to both the user interface and storage circuitry. According to one embodiment, the user interface can be coupled to structure 12a and provide user access to the process circuitry. The user interface can take the form of a keyboard, a keypad, and/or a touch screen aligned with the exterior of the structure in exemplary embodiments and the user interface can be within the volume defined by structure 12a when structure 12a houses components 14a. Access to the user interface can be had through access panels, doors or openings (not shown) in structure 12a, for example. In other embodiments, the user interface can be a computer interface that is configured to provide access to another process and control component, for example a stand alone computer. In exemplary embodiments, the computer interface can be a wireless interface and in other embodiments, the computer interface can take the form of a TCP/IP or a standard LAN connection. In exemplary embodiments, instrument 10a can be configured to accumulate and store sample data unattended. In other embodiments, instrument 10a can be configured to allow access to data and further provide for the manipulation of the data acquired. According to another embodiment, instrument 10a can be configured to send data to a remote computer upon acquisition.

In one embodiment, the progression of analysis from inlet system component 16 to detection component 18 can be controlled and/or monitored by the processing circuitry of process and control component 19. The processing circuitry may be implemented as a processor or other structure configured to execute executable instructions including, for example, software and/or firmware instructions. Other exemplary embodiments of the processing circuitry include hardware logic, PGA, FPGA, ASIC, and/or other structures. These examples of the processing circuitry are for illustration, and other configurations are possible.

The processing circuitry can be configured to control the values of analytical component parameters defined by the user of the instrument and/or monitor the components. Control of the analytical component parameter values by the processing circuitry can include, for example, dictating a predefined temperature program to perform gas chromatography by inlet system component 16. In one embodiment, the processing circuitry can also be configured to control the sample introduction port of component 16. Exemplary monitoring includes the recording of data received from detection component 18. By varying analytical component parameter values utilized, sample characteristics and/or data can be obtained, typically in the form of a chromatogram.

In one aspect, the processing circuitry may execute data acquisition and searching programming and/or be configured to perform data acquisition and searching that includes the acquisition of sample characteristics such as total ion current and/or mass spectra. In another aspect, the processing circuitry can be configured to associate chromatograms associated with the analysis of a previously identified sample (known) with a sample currently under analysis (unknown). For example, the processing circuitry can be configured to store and access data from the storage circuitry. The storage circuitry can be configured to store electronic data and/or programming such as executable instructions (e.g., software and/or firmware), data, or other digital information, and may include processor-usable media. The processor-usable media can include any article of manufacture which can contain, store, or maintain programming, data and/or digital information for use by or in connection with an instruction execution system including processing circuitry, in the exemplary embodiment. For example, exemplary processor-usable media may include any one of physical media such as electronic, magnetic, optical, electromagnetic, and infrared or semiconductor media. Some more specific examples of processor-usable media include, but are not limited to, a portable magnetic computer diskette, such as a floppy diskette, zip disk, hard drive, random access memory, read only memory, flash memory, cache memory, and/or other configurations capable of storing programming, data, or other digital information. Embodiments also include configurations where process and control components 19 can be configured to acquire sample data and analyze acquired data unattended.

For example, component 16 can be configured as an autosampler and in exemplary embodiments air and/or liquid samples can be acquired at predefined intervals as dictated by process and control component 19. Process and control component 19 can be configured according to predefined user parameters to acquire sample data. In other embodiments, process and control component 19 can be configured to forward data and/or instrument status to remote locations via wireless and/or wired communication.

Figure 3:
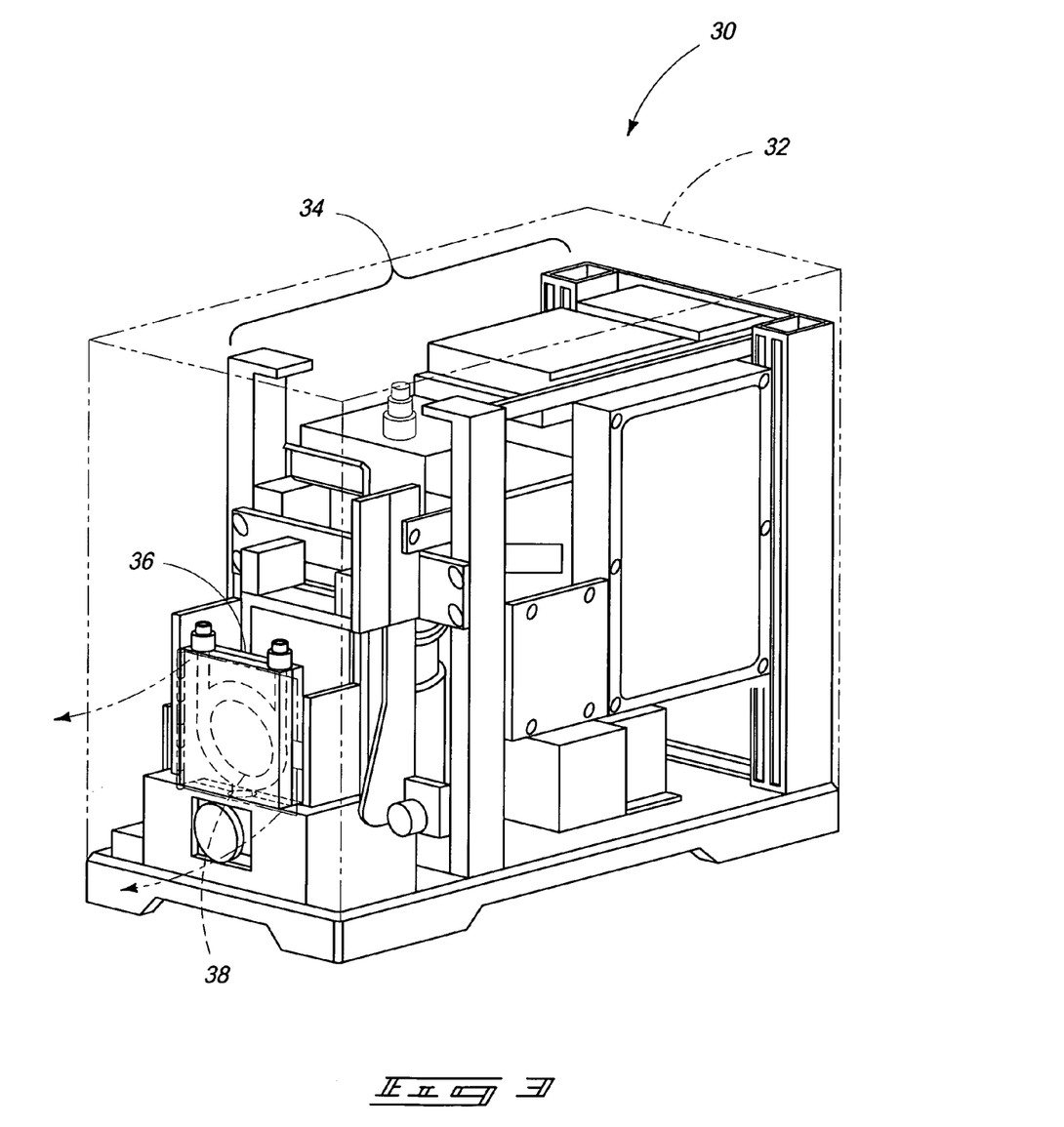
FIG. 3 is an isometric view of the instrument of FIG. 1 according to an embodiment.

Referring to FIG. 3, instrument 30 is depicted according to an exemplary embodiment. Instrument 30 can include support structure 32 as well as analytical components 34. More particularly, analytical instrument 30 can include a gas chromatography apparatus 36 and, as exemplarily shown, support structure 32 of instrument 30 can include an access panel 38 to allow access to apparatus 36. Apparatus 36 is exemplary of a sample preparation component of component 16 described herein and can be utilized according to other instrument configurations beyond the may examples given herein as will be obvious to those of ordinary skill in the analytical arts.

Figure 4:
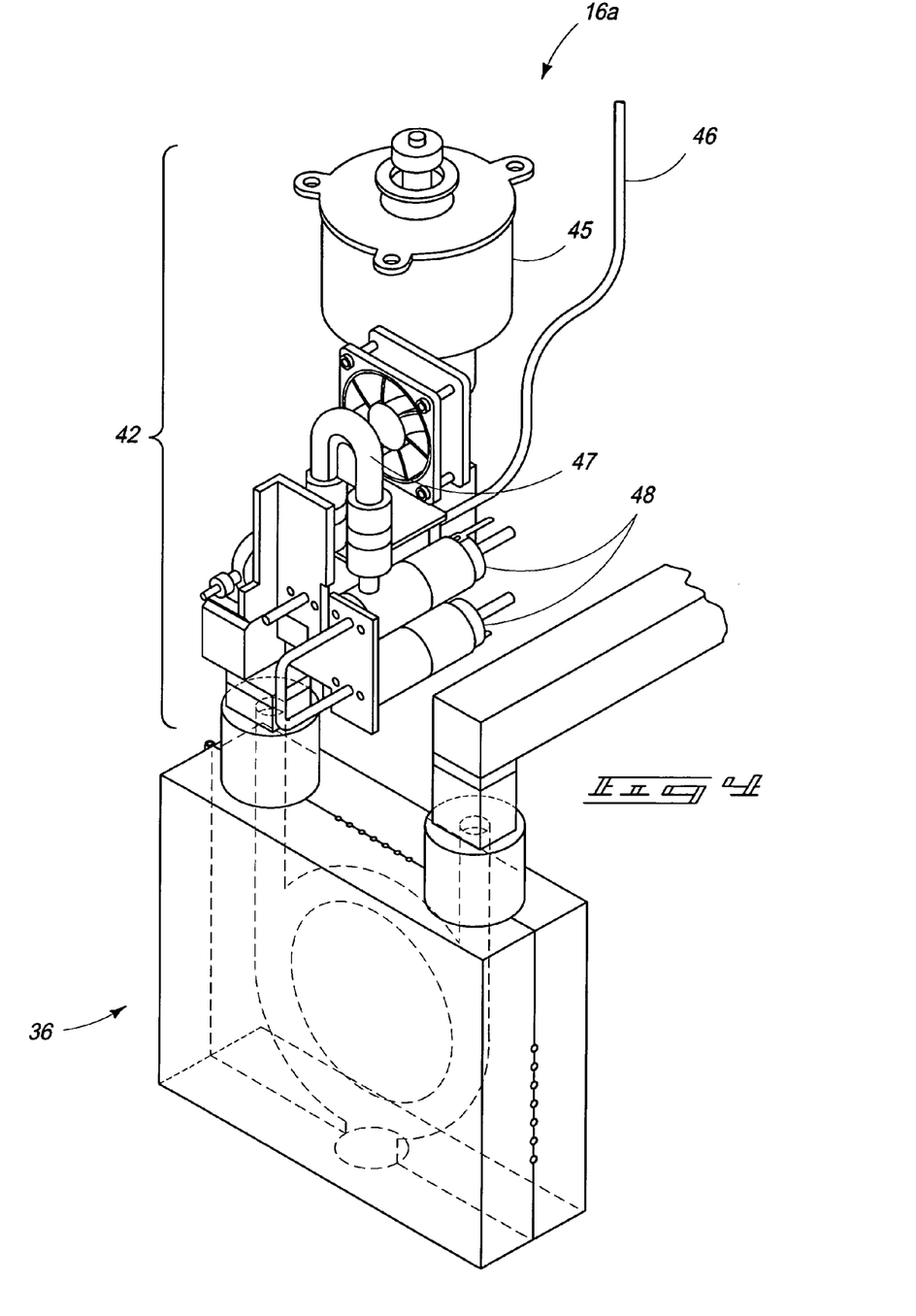
FIG. 4 is an isometric view of components of the instrument of FIG. 1 according to an embodiment.

Referring to FIG. 4, component 36 can be coupled to other sample introduction components 16a, for example. Components 16a can include sample introduction components 42 and chromatography apparatus 36, for example. Component 42 can include an interface that includes a continuous air sampling system 46, for example. System 46 can include a diaphragm sampling pump that is configured to pull ambient air through a preconcentrating sorbent material 47. The sorbent material can be configured to preferentially trap compounds of interest while allowing compounds of less interest, in certain applications, for example, nitrogen and oxygen, to pass through. In an exemplary embodiment, system 46 can include a heater that can be configured to rapidly desorb the compound of interest onto the head of a chromatography column within chromatography component 36. In exemplary embodiments, switching valves 48 can be utilized in conjunction with the process and control components to control the flow of sample and/or carrier gas through sorbent material in conjunction with the predefined heating of the sorbent. Components 42 can include heated transfer lines to efficiently deliver a sample from component 46. Components 42 can also include a direct injection interface 45 that allows for direct analysis of samples and/or can allow for the preparation of calibration curves utilizing the process and control components.

Figure 5:
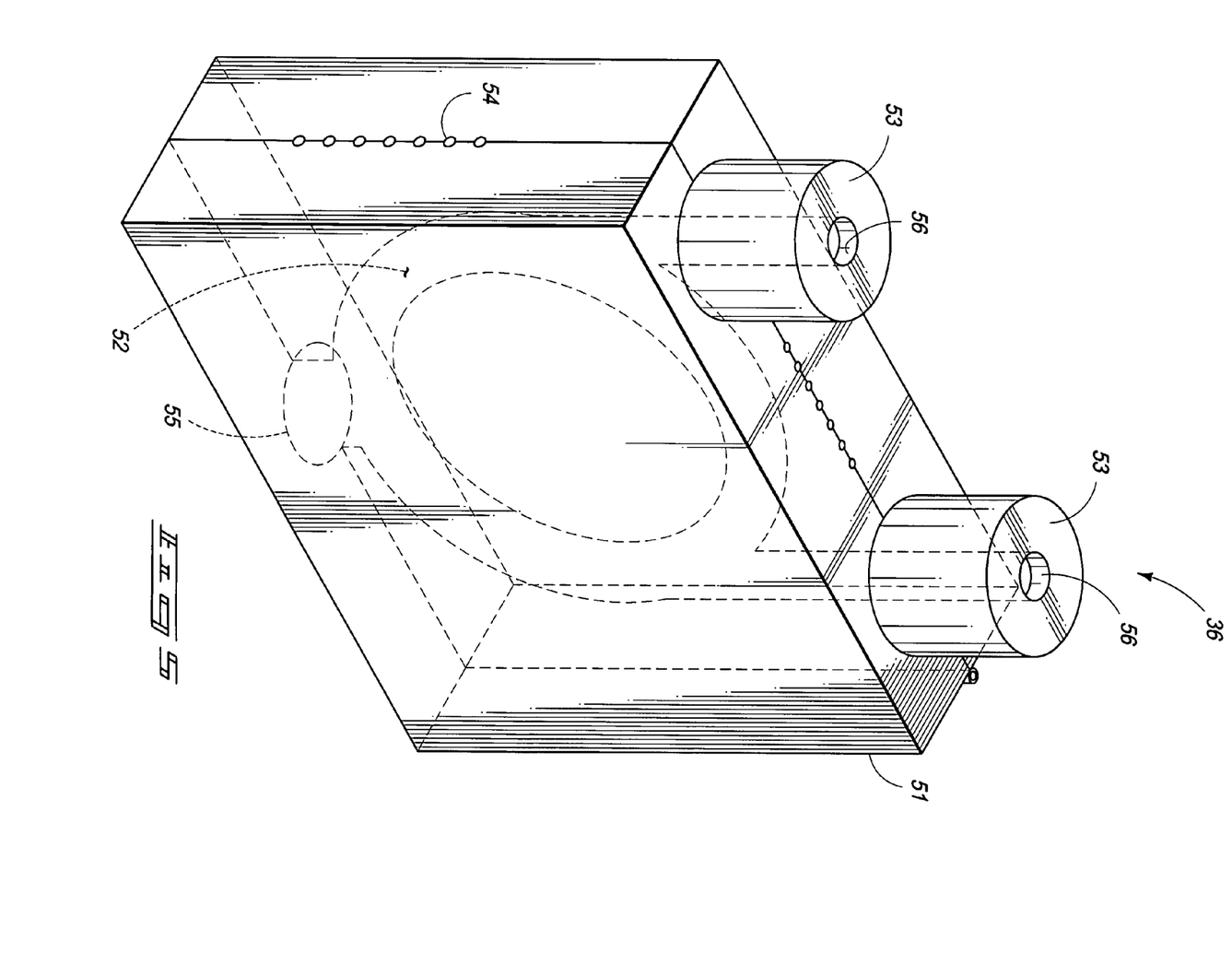
FIG. 5 is an isometric view of a component of the instrument of FIG. 1 according to an embodiment.

Referring to FIG. 5, apparatus 36 is shown in a first operable position or closed configuration. Apparatus 36 can include a housing 51 defining at least one compartment 52 therein. Compartment 52 can be configured to receive a gas chromatography column, for example. Housing 51 can be configured to substantially envelop the column within compartment 52. According to exemplary embodiments the column can be enveloped through covering all sides of the column with walls of compartment 52. For example, and by way of example only, the column can be configured as a capillary gas chromatography column and all exterior walls of the column, including walls that traditionally oppose one another in state of the art chromatography apparatuses, oppose wall of compartment 52 in apparatus 36.

Compartment 52 can be configured to substantially conform to the outline of a gas chromatography column. For example, commercially available capillary columns typically are configured in a circle. Compartment 52 can be configured to receive these columns configured as commercially available, such as columns configured in a circle. Compartment 52 can be configured to receive columns and provide for minimal air space between the column and the walls of compartment 52. For example, compartment 52 can be configured to receive a column without the column physically contacting the walls of the compartment. According to exemplary embodiments, compartment 52 can have a volume less than 100 mL or even less than 50 mL. Compartment 52 can be configured to have a volume sufficient to receive columns of various lengths and diameters while providing a minimal amount of air volume when the column is received within compartment 52.

The columns can be at least 1 M in length; from 5 to 30M in length; and at least 30 M in length, for example. The volume of compartment 52 can be less than about 100 mL, and according to exemplary embodiments, compartment 52 can have a volume of less than 50 mL to accommodate these columns.

Apparatus 36 includes first and second connectors 56 coupled to housing 51. According to exemplary embodiments, the first connector can be configured to couple a sample preparation component to the column within compartment 52, and the second connector can be configured to couple a detection component to the column within compartment 52. This coupling can be preformed using coupling devices such chromatography column fittings known in the art.

According to exemplary embodiments, compartment 52 defined by the housing can be substantially tubular. Compartment 52 defined by the housing can also be substantially circular in at least one cross section. Compartment 52 defined by the housing can be configured as a tunnel extending from the first connector to the second connector. According to exemplary embodiments, at least a portion of the tunnel extending from the first connector to the second connector can be configured to form a complete circle within the housing. An exemplary implementation of compartment 52 is a tunnel having at least a portion extending from the first connector to the second connector and forming a semi-circle within the housing.

Apparatus 36 can also include a plurality of vents 54 extending from exterior portions of housing 51 to compartment 52. Vents 54 can be configured to provide a tortured path for atmosphere to either enter or depart compartment 52. For example, during a cooling cycle of apparatus 36 it may be desired to remove atmosphere from within compartment 52 by providing a pressure differentiation at opening 55. According to exemplary embodiments, a pressure differentiating component can be coupled to compartment 52 via opening 55 extending from compartment 52 through an exterior surface of housing 51. Opening 55 can be configured to provide fluid communication between compartment 52 and the pressure differentiating component. The pressure differentiating component can be a vacuum pump and/or a fan. This pressure differentiation may be provided using a fan to force gas into compartment 52 or draw atmosphere from compartment 52. Vents 54 may be configured to allow atmosphere to pass into or out of compartment 52 at a desired rate. According to exemplary embodiments, the pressure differentiating component can be a cooling fluid such as compressed carbon dioxide and/or nitrogen.

Pumps used to transfer atmosphere into or out of compartment 52 may be configured to support another component of the analytical instrument. For example, the pump may also be utilized to facilitate the operation of other analytical components such as a mass spectrometry component.

In an exemplary implementation, the pump may be configured to provide for the exchange of the atmosphere within compartment 52. For example, the processing and control components may be configured to initiate the removal of the atmosphere from compartment 52 and upon removal another atmosphere may enter compartment 52 via vents 54. The atmosphere entering compartment 52 via vents 54 may have a lower temperature than the atmosphere being removed from compartment 52. Such exchange can result in the cooling the contents of compartment 52, specifically the column within compartment 52. In exemplary embodiments, the size and/or shape of vents 54 may dictate the speed and/or accuracy with which the temperature within compartment 52 may be changed and/or maintained.

According to another exemplary implementation, a composition may be provided to compartment 52 to facilitate cooling of the contents of compartment 52. For example, the composition provided to compartment 52 may be in the liquid form, such as liquid nitrogen, and/or the composition may be in the gaseous form, such as nitrogen, carbon dioxide, and/or air. The providing of the composition to compartment 52 can be facilitated by establishing a pressure differential across vents 54. This differential can be achieved by providing the composition to the exterior of vents 54 having a higher pressure than the interior of compartment 52, for example. Such composition may be provided in the form of compressed gas, for example, and/or may be provided from another component of the instrument. For example, where the inlet system to the instrument includes a split/split-less injection component, the split from the injection component may be provided to the exterior of vents 54. In exemplary embodiments, the split may be transferred to the vents via tubing having a coil and/or grid. The coil and/or grid may be placed proximate a cooling unit such as a fan. As the split transverses the coil and/or grid, the gas within the tubing may be cooled before proceeding to vents 54, for example. It is also contemplated that the composition can be provided to the exterior of vents 54 and vacuum drawn on opening 55 to facilitate a pressure differential across vents 54.

Figure 6:
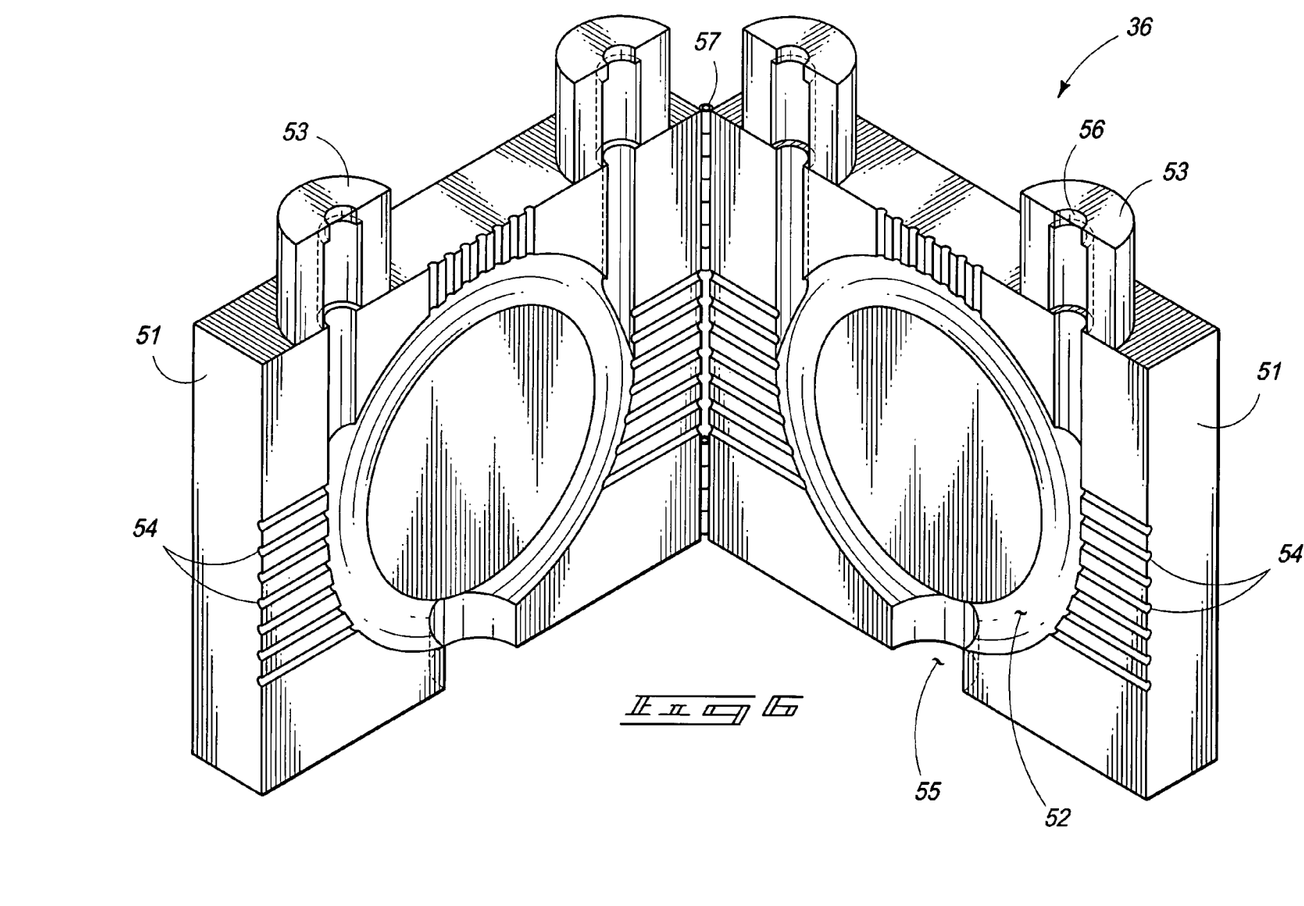
FIG. 6 is an isometric view of the component of FIG. 5 according to an embodiment.

Referring to FIG. 6, apparatus 36 is depicted in a second, open, operable position allowing access to compartment 52. According to an exemplary embodiment apparatus 36 can include at least two pieces of material. Each of the pieces of material can have surfaces configured to interface with one another and define compartment 52 when in the first operable position depicted in FIG. 5, for example. According to exemplary embodiments a surface of at least one of the pieces of material and/or or both pieces of material can define an opening within either or both surfaces. The opening can define at least a portion of compartment 52 when the surface of one piece of material interfaces with the surface of the other piece of material, for example when apparatus 36 is in the first operable position. A surface of either one or both pieces of material can define vents 54 as well. According to exemplary embodiments the openings defined by the surface of either or both pieces of material that define compartment 52 can substantially compliment an outline of a gas chromatography column. According to exemplary embodiments, this column can be a capillary column in its traditional coiled configuration. The opening may also compliment a circular column. According to exemplary embodiments, the opening defined by the surface can include a trench extending from the first connector to the second connector. The trench can be concave in at least one cross section.

As depicted in FIG. 6, apparatus 36 can be configured of multiple pieces of material. According to exemplary embodiments, at least two of these pieces of material can be operably coupled to one another. For example an end of one piece of material can be coupled to one end of another piece of material via a hinge. According to exemplary embodiments, the pieces can be configured to be positioned in a first operable position to substantially envelop the column, and a second operable position wherein the pieces are spaced from one another sufficient to access compartment 52 and/or a column. The first operable position can be considered the closed position and the second operable position can be considered the open position.

Compartment 52, in an exemplary embodiment, has been machined and/or etched into the two parts of housing 51. Likewise vents 54 are shown machined and/or etched into the two parts of housing 51. This hinge configuration is but one of the many exemplary configurations of component 36 of the present description.

Figure 7:
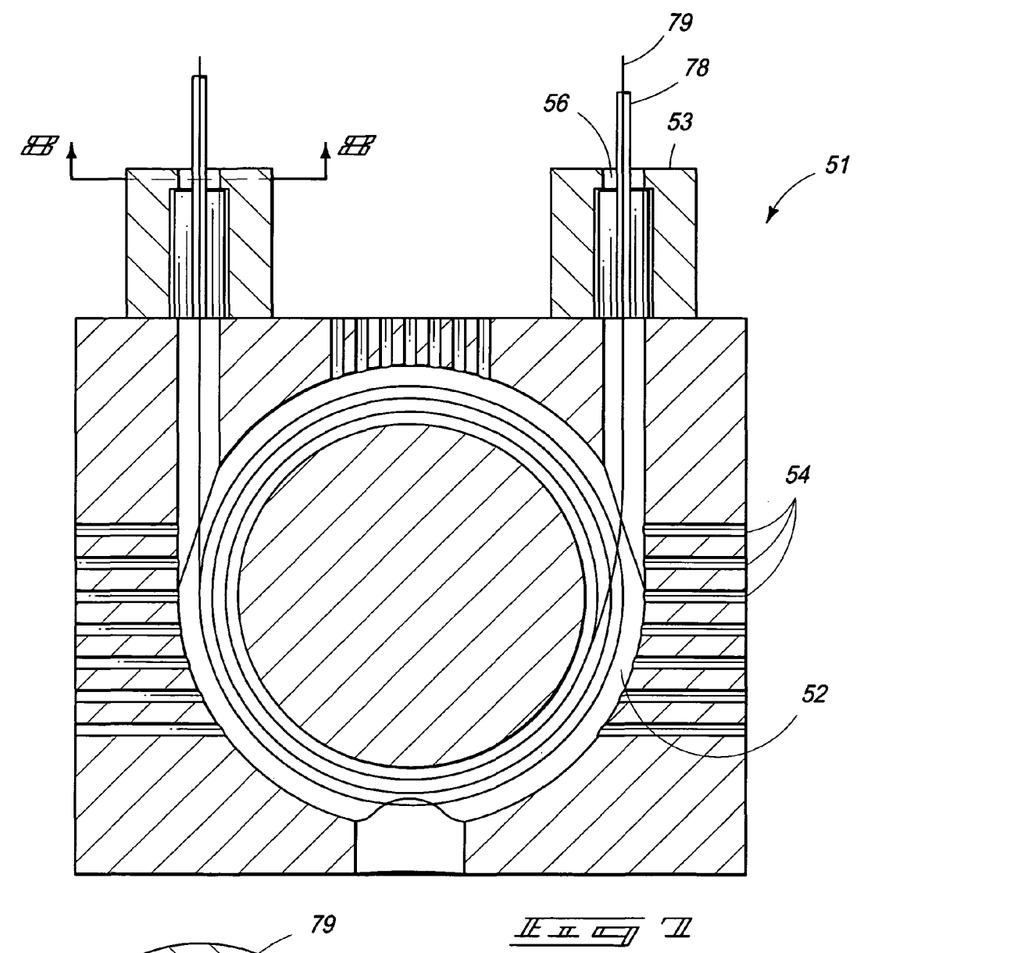
FIG. 7 is an elevational view of the component of FIG. 5 according to an embodiment.
Figure 8:
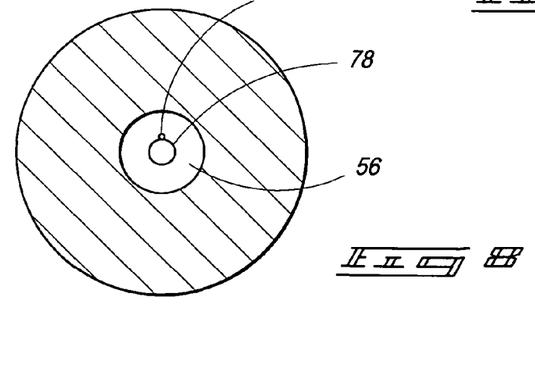
FIG. 8. is a cross-sectional view of the component of FIG. 7 according to an embodiment.

Referring to FIGS. 7 & 8, an elevational cross section of housing 51 is shown having an isolated heater 78 therein as well as an exemplary capillary gas chromatography column 79. Apparatus 36 can include compartment 52 configured to receive a heating element, for example. The heating element can be configured to extend from the first connector through compartment 52 to the second connector.

According to exemplary embodiments, compartment 52 can be configured to receive both a chromatography column and a compartment heater. Compartment 52 can be configured to receive a compartment heater and align the column received to allow for the majority of the column to reside in the heated zone provided by the heater. For example, the heater can be within the space between the column and the walls of compartment 52. According to exemplary implementations, the heater can reside in the compartment without physically contacting the column. Other implementations include the heater residing within compartment 52 without physically contacting the walls of the compartment and/or the column. In accordance with other aspects of the disclosure, the heater can be incorporated into the walls of the compartment. According to exemplary implementations, the heater can provide a heated zone within compartment 52. This heated zone can extend throughout an entirety of the volume defined by compartment 52. In accordance with exemplary implementations, a majority and/or an entirety of the column received by compartment 52 can be within this heated zone.

The alignment of the heater 78 and the column 79 is depicted within opening 56, for example. Opening 56 can be configured to provide for the sealing of heater 78 and column 79 within opening 56. Typical heaters are low-thermal-mass resistive heaters that can be electrically isolated from an outer shell such as housing 51. Exemplary heaters 78 include those of aluminum and those that can be used as a heat sink. Referring to FIG. 7, heater 78 is electrically isolated from column 79 within compartment 52 by a heat sink material such as aluminum. Heater 78 can be configured to distribute heat uniformly within compartment 52. In exemplary embodiments, the heat sink material can shield heater 78 from housing 51 as well. Column 79 can reside within the heat sink provided by heater 78. In exemplary embodiments, the low dead volume, such as the less than 50 mL discussed above, combined with a low thermal mass of a heat sink can allow for a temperature ramp rate of at least 60° C. per minute with from between about 10 W of power to about 40 W of power from power supply 20. Application of more power can result in higher temperature ramp rates. For example, power greater than 40W can result in ramp rates greater than 60° C. per minute as desired by the operator. Ramp rates as high as 300° C./min can also be achieved. Ramp rates can also be configured to account for the thermal mass of the chromatography column utilized. For example, a higher ramp rate per unit of power can be achieved using a 5 meter capillary column as compared to a ramp rate per unit power when utilizing a 30 meter column. Exemplary columns include those between 1 meter and 30 meters.

In exemplary embodiments, the atmosphere within compartment 52 can be cooled rapidly a pressure differentiation device as exemplarily described herein. Utilizing the process and control components in conjunction with the power supply and heater 78 as well as pressure differentiation for example, forced convection cooling and/or heating may be obtained and utilized to maintain and/or modify the temperature of the atmosphere within compartment 52 and hence column 79.

Figure 9:
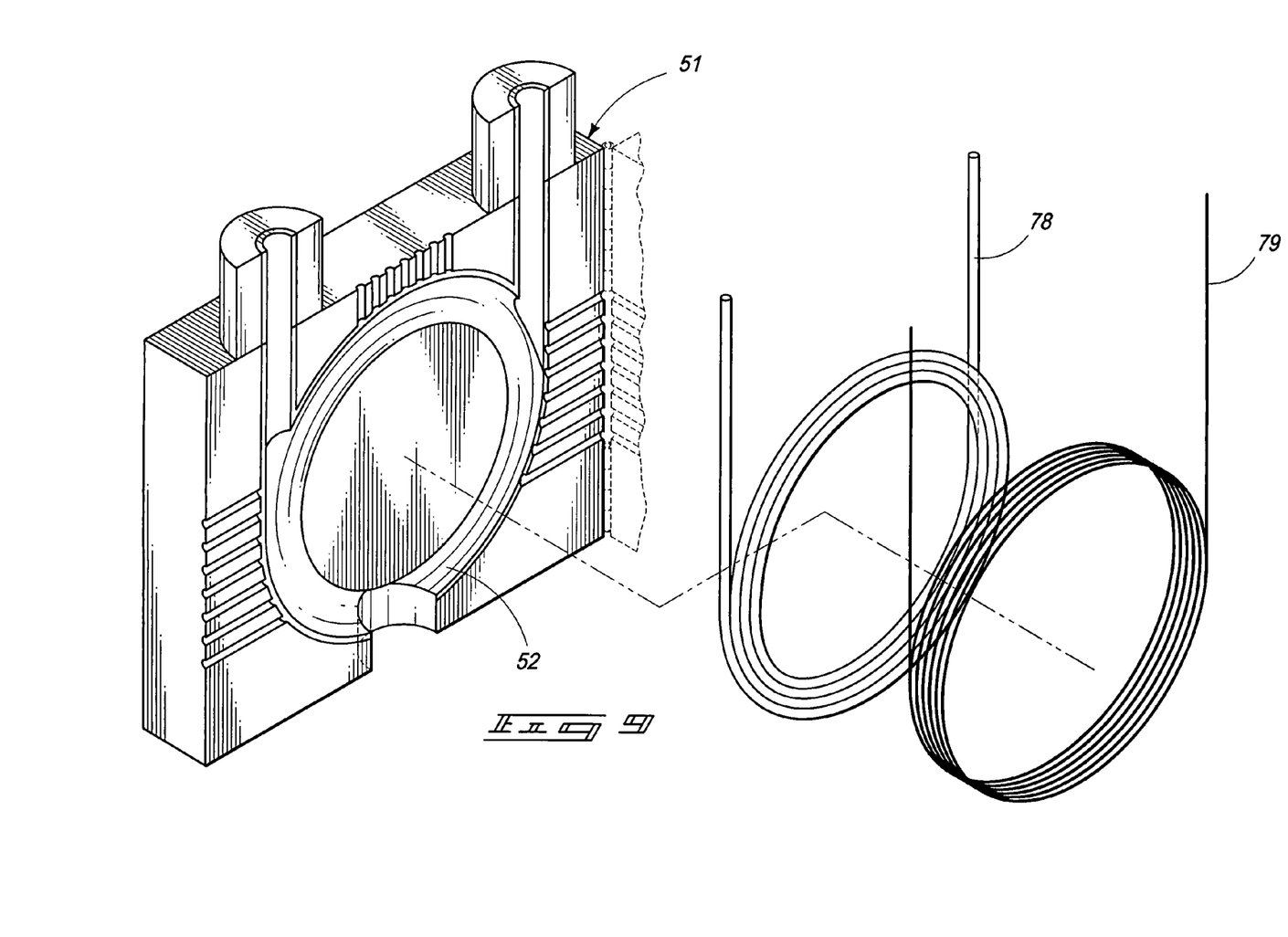
FIG. 9 is an exploded view of the component of FIG. 7 according to an embodiment.

With reference to FIG. 9, an exemplary exploded depiction of the placement of column 79 and heater 78 within a part of housing 51 is shown. As shown, heater 78 can be placed proximate housing 51 in an exemplary embodiment. As described, between heater 78 and column 79 may exist a heat sink material (not shown). In the exemplary embodiment, column 79 is separate from heater 78 and may be separated from housing 51 for maintenance and/or replacement as the operator requires. By way of another example, compartment 52 may be configured to house more than one heater 78.

Figure 10:
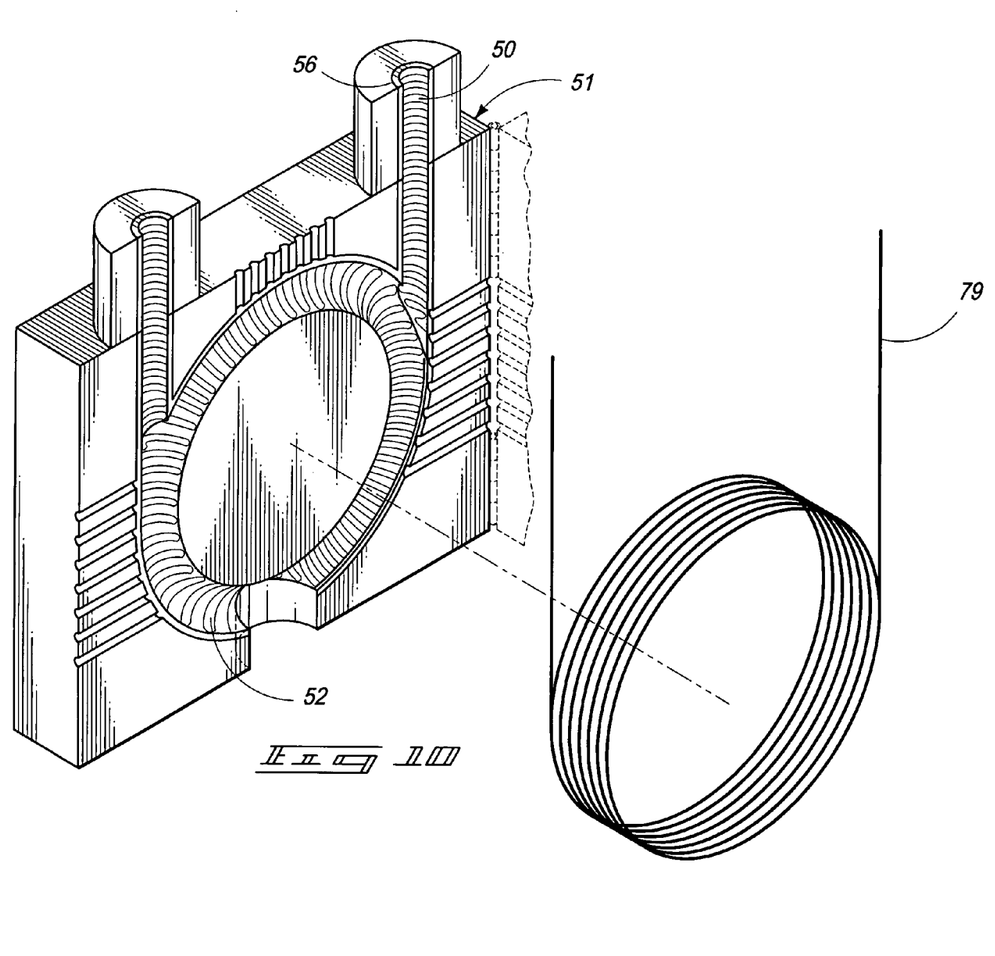
FIG. 10 is an exploded view of a component of the instrument of FIG. 1 according to an embodiment.

Referring to FIG. 10, housing 51 can be configured with a heater construction 50. In exemplary embodiments, construction 50 can include a serial array of coated wires within and/or along the sidewalls of compartment 52. This array can be dispersed throughout the interior walls of compartment 52 on either or both sides of housing 51 and/or along the sidewalls of openings 56. The density of the array can be distributed as desired to account for heat sinks within or proximate compartment 52. For example, near connectors 53 within compartment 52, the array can be more dense than along the sidewalls of compartment 52 to account for additional heat sink that may result from connectors 53. As another example, the density of the array can be decreased to provide a region within the compartment having a temperature profile different from that in the remainder of the compartment. In exemplary applications, as configured with such a region, the instrument may be utilized to perform a modified GC analysis. As depicted in FIG. 10, column 79 can be placed within compartment 52 having construction 50 encompassing the interior of compartment 52.

Figure 11:
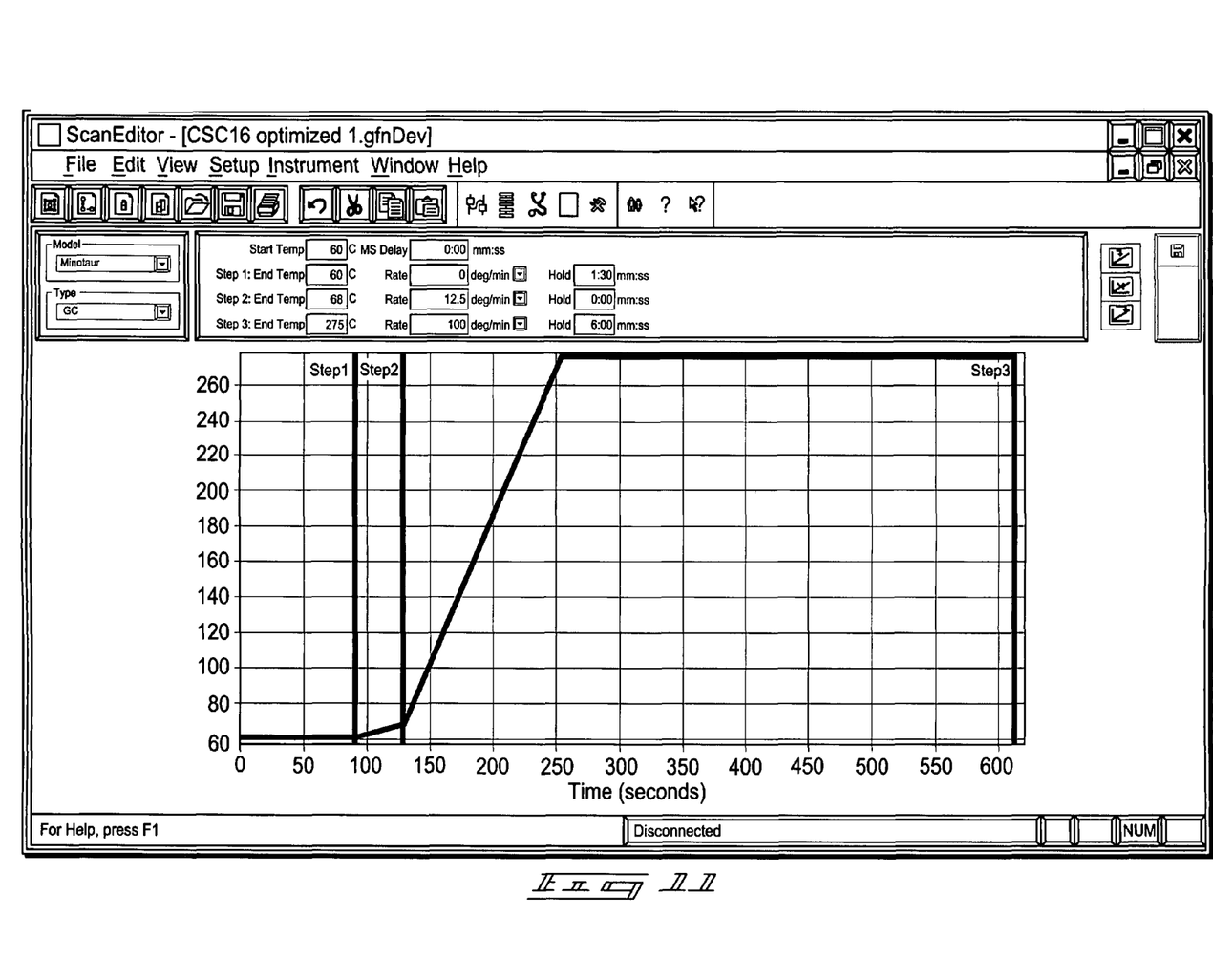
FIG. 11 is an exemplary gas chromatography program according to an embodiment.

Referring to FIG. 11, an exemplary chromatography program is illustrated. The chromatography program may be utilized by the process and control components in conjunction with the analytical components described herein. In exemplary embodiments, compartment 52 may be sealed under vacuum when elevating the temperature of the heaters. When heating under vacuum in this configuration, rapid heating profiles can be achieved.

According to exemplary implementations, apparatus 36 can be used to complete analytical methods. For example, a sample can be provided to a gas chromatography column. The sample can include a plurality of components. The temperature of the column can be increased at a rate of about 60° C./minute using less than about 40 W to separate one of the components from at least one other component of the sample. According to exemplary embodiments, the temperature of the column can be increased at a rate of about 60° C./minute using from about 10 W to about 40 W. Methods can also include decreasing the temperature of the column by contacting the column with a cooling fluid such as carbon dioxide and/or nitrogen.

The analytical methods can also include providing at least one gas chromatography column compartment configured to substantially envelop a gas chromatography column with the one compartment being comprised of at least a first portion operably coupled to a second portion. The portions can define the one compartment in a first operable position and allowing access to the one compartment in a second operable position. According to exemplary embodiments, analysis can be performed with the one compartment in the first operable position. The portions can then be transitioned to the second operable position to allow access to the one compartment. According to exemplary embodiments, the first portion can be operably coupled to the second portion via a hinge.

Methods can also include removing one column from the compartment after transitioning the portions to the second operable position as well as replacing the one column with another column after removing the one column.

Exemplary methods of producing apparatus 36 can include providing a first substrate comprising a first surface extending to opposing edges. Substrates of apparatus 36 can be a relatively solid structure such as a lightweight material in one embodiment and/or, in other embodiments, a material that provides low thermal conductivity such as an insulative material. One exemplary material of construction for the substrate 51 is Zircal 18 (available from Zircar Refractory Components, Inc. Florida, N.Y., 10921, USA), which is typically a ceramic that may be machined.

According to exemplary embodiments a first trench can be formed within the first surface of the substrate. The substrate of apparatus 36 can be machined to provide compartment 52 within apparatus 36. The trench can be machined to provide sufficient space to house a gas chromatography column. Chromatography columns that may be housed within compartment 52 include both capillary and non-capillary chromatography columns. The chromatography columns may be acquired "off the shelf" from commercial vendors such as RESTEK (110 Benner Circle, Bellefonte, Pa. 16823), for example.

In exemplary embodiments, compartment 52 can be less than 50 mL in dead air volume and/or compartment 52 can be machined from two separate pieces which can be used to form apparatus 36. In accordance with exemplary implementations, the first substrate can be aligned with a second substrate to define compartment 52 between the first and second substrates. Compartment 52 can be configured to substantially envelop a gas chromatography column as described, for example. The trench of the first substrate, for example, can extend from one of the opposing edges of the first substrate through the first substrate to the same opposing edge. The trench can be configured as a semi-circle within the substrate or a circle within the substrate. According to exemplary embodiments, a second trench can be formed with the second substrate. The second trench can be configured to further define compartment 52 upon aligning the first substrate with the second substrate. The first substrate can also be operably coupled to the second substrate.

The invention claimed is:

1. An analytical instrument comprising a sample preparation component coupled to a gas chromatography apparatus, and a detector component coupled to the gas chromatography apparatus, wherein the chromatography apparatus comprises:
    a housing comprised by at least two complimentary portions, each of the portions defining a circuitous recess as well as sets of channels extending between the circuitous recesses and an edge of the portions, when the portions are operatively engaged, the recesses of the portions define at least one chromatography column compartment, and the channels of the portions define a plurality of vents, wherein the volume of the at least one chromatography column compartment is less than 100 mL and individual vents extend to individual edges of the portions, a plurality of the edges defining a portion of the vents.

2. The analytical instrument of claim 1 wherein at least some of the vents are aligned opposing one another in one cross section.

3. The analytical instrument of claim 1 further comprising chromatography coupling openings extending from the at least one chromatography column compartment to one edge of the housing.

4. The analytical instrument of claim 3 further comprising at least one pressure differentiating opening extending from the at least one chromatography column compartment to another edge of the housing, the one edge of the housing opposing the other in one cross section.

5. The analytical instrument of claim 1 further comprising at least one pressure differentiating opening extending from the at least one chromatography column compartment to one edge of the housing.

* * * * *

UNITED STATES PATENT AND TRADEMARK OFFICE
CERTIFICATE OF CORRECTION

| | | |
|---|---|---|
| PATENT NO. | : 8,043,565 B1 | Page 1 of 1 |
| APPLICATION NO. | : 11/433240 | |
| DATED | : October 25, 2011 | |
| INVENTOR(S) | : Garth E. Patterson and Mark A. Gregory | |

It is certified that error appears in the above-identified patent and that said Letters Patent is hereby corrected as shown below:

Column 6, lines 50-51 – Replace "Ser. No. 11/919,323 filed May 10, 2006" with --Ser. No. PCT/US2006/015948 filed April 25, 2006--

Column 8, line 19 – Replace "may examples" with --many examples--

Column 9, line 23 – Replace "such chromatography" with --such as chromatography--

Column 10, line 5 – Replace "cooling the" with --cooling of the--

Column 10, line 44 – Replace "and/or or both" with --and/or both--

Column 11, line 65 – Replace "account the" with --account for the--

Signed and Sealed this
Eighteenth Day of September, 2012

David J. Kappos
*Director of the United States Patent and Trademark Office*